United States Patent
Nakata et al.

(10) Patent No.: US 6,833,358 B1
(45) Date of Patent: Dec. 21, 2004

(54) LACRIMAL SECRETION PROMOTERS OR EYE DROPS FOR TREATING KERATOCONJUNCTIVAL FAILURE CONTAINING AS THE ACTIVE INGREDIENT NATRIURETIC PEPTIDES

(75) Inventors: Katsuhiko Nakata, Ikoma (JP); Masatsugu Nakamura, Ikoma (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/787,164

(22) PCT Filed: Sep. 24, 1999

(86) PCT No.: PCT/JP99/05239

§ 371 (c)(1),
(2), (4) Date: Apr. 9, 2001

(87) PCT Pub. No.: WO00/18422

PCT Pub. Date: Apr. 6, 2000

(30) Foreign Application Priority Data

Sep. 28, 1998 (JP) .............................. 10-273332

(51) Int. Cl.$^7$ ............................................ A61K 38/00
(52) U.S. Cl. ................................ 514/21; 514/2; 514/12; 424/78.02; 424/78.04
(58) Field of Search ................................. 514/12, 2, 21; 424/78.02, 78.04

(56) References Cited

U.S. PATENT DOCUMENTS

| | | | | |
|---|---|---|---|---|
| 4,452,818 A | * | 6/1984 | Haidt | ............... 424/352 |
| 4,748,232 A | | 5/1988 | Matsuo et al. | |
| 5,252,318 A | * | 10/1993 | Joshi et al. | .......... 424/78.04 |
| 5,434,133 A | * | 7/1995 | Tamaka et al. | ............... 514/12 |
| 5,441,732 A | * | 8/1995 | Hoeg et al. | ............. 424/78.04 |
| 5,583,108 A | * | 12/1996 | Wei et al. | ............... 514/12 |
| 5,767,239 A | * | 6/1998 | Immer et al. | ............... 530/339 |

FOREIGN PATENT DOCUMENTS

| EP | 0 385 476 A | | 9/1990 | |
|---|---|---|---|---|
| EP | 385476 | * | 9/1990 | ........... C12P/21/02 |
| EP | 0 466 174 A | | 1/1992 | |
| EP | 466174 | * | 1/1992 | ........... C12P/21/02 |
| JP | 10-218792 A | * | 8/1998 | .......... A61K/45/00 |
| JP | 10-236972 A | | 9/1998 | |
| JP | 10-236972 | * | 9/1998 | .......... A61K/38/00 |

OTHER PUBLICATIONS

Lange et al. Localization of atrial natriuretic peptide/cardiodilatin (ANP/CDD)—Immunoreactivity in the lacrimal gland of the domestic pig. Exp. Eye Res. (1990) 50: 313–316.*

W. Lange et al. Localization of Atrial Natriuretic Peptide/Cardiodilatin (ANP/CDD)—Immunoreactivity in the lacrimal Gland of the Domestic Pig. Exp. Eye Res. 313–316 (1990).

Keiko Ofuji et al, "Current Treatment of Dry Eye", Journal of the Eye, 11(8), pp. 1179–1185 (1994) (with English language *Abstract*).

"Peptides Adjusting Circulation and Related Diseases", Youdosha, pp. 14–25 (1992) (with English language *Abstract*).

K. Takada: Nippon Medical School CCU, et al, Jpn. Pharmcol. Ther., 23, pp 949–952 (1995) (with English language *Abstract*).

T.W. Mittag et al, "Atrial natriuretic peptide (ANP), guanylate cyclase, and intraocular pressure in the rabbit eye", Current Eye Research, vol. 6, No. 10, pp. 1189–1196 (1987).

* cited by examiner

*Primary Examiner*—Christopher R. Tate
*Assistant Examiner*—Maury Audet
(74) *Attorney, Agent, or Firm*—Frishauf, Holtz, Goodman & Chick, P.C.

(57) ABSTRACT

The object of the present invention is to find new effects of natriuretic peptides in an ophthalmological field. The present invention provides eyedrops for promoting lacrimal secretion or for treating keratoconjunctival disorders containing the natriuretic peptide as active ingredient. The natriuretic peptides are atrial natriuretic peptides (ANP), brain natriuretic peptides (BNP) and C-type natriuretic peptides (CNP). Typical examples of the keratoconjunctival disorder are dry eye, corneal erosion and corneal ulcer.

10 Claims, No Drawings

LACRIMAL SECRETION PROMOTERS OR EYE DROPS FOR TREATING KERATOCONJUNCTIVAL FAILURE CONTAINING AS THE ACTIVE INGREDIENT NATRIURETIC PEPTIDES

This application is the United States National Phase Application under 35 USC 371 of International Application PCT/JP99/05239 (not published in English) filed Sep. 24, 1999.

TECHNICAL FIELD

The present invention relates to eyedrops for promoting lacrimal secretion or treating keratoconjunctival disorders containing a natriuretic peptide as an active ingredient.

BACKGROUND ART

A lacrimal fluid, which has a mechanism to retain wettability on living bodies, covers cornea and conjunctiva (keratoconjunctiva), retains wettability and prevents them from drying. The lacrimal fluid works as a lubricant protecting the keratoconjunctiva from stimulation by blinking and contributes to retaining smoothness of the corneal surface. The lacrimal fluid has bacteriostasis, prevents infection from bacteria, fungus, virus and the like, supplies oxygen and a variety of nutrition to the cornea and removes a carbon dioxide gas and metabolites. When the keratoconjunctiva is disordered, the lacrimal fluid plays a role to dilute and remove disordering stimuli, and works to carry liquid components such as epidermal growth factors participating in wound healing and hematocyte components such as fibronectin to disordered sites. That is, the lacrimal fluid participates in adjusting wound healing as well as retaining keratoconjunctival epithelial cells. Thus, it is known that the lacrimal fluid, though its amount is very small, adjusts a physiological condition of the keratoconjunctiva, and thereby maintaining transparency and homeostasis of the cornea (Journal of the Eye, 11, 1179–1185 (1994)).

Known methods of treating keratoconjunctival disorders such as dry eye (keratoconjunctivitis sicca and the like) are a method of supplying lacrimal fluid components with artificial tears, a method of retaining a lacrimal fluid remaining on the keratoconjunctiva surface with a viscoelastic substance to lead to treating the keratoconjunctiva and the like. Since the lacrimal fluid exhibits the above-mentioned effect of curing the keratoconjunctival disorders, it is expected that finding compounds acting on a lacrimal gland function directly and promoting lacrimal secretion is useful for curing corneal erosion, corneal ulcer and the like having keratoconjunctival epithelial disorders such as dry eye.

Peptides belonging to natriuretic peptides are widely distributed in mammal, birds, amphibians and fish and are classified into three groups, namely atrial natriuretic peptides (ANP), brain natriuretic peptides (BNP) and C-type natriuretic peptides (CNP), according to structure. Known atrial natriuretic peptides (ANP) are α-ANP consisting of 28 amino acids, α-ANP [4–28] consisting of 4th to 28th amino acids of α-ANP, α-ANP [5–28] consisting of 5th to 28th amino acids of α-ANP, β-ANP having an antiparallel dimer structure of α-ANP, high-molecular type γ-ANP having molecular weight of 13,000 formed by cutting out a signal peptide from an ANP precursor and the like. Known brain natriuretic peptides (BNP) are BNP-26 consisting of 26 amino acids, BNP-32 consisting of 32 amino acids, BNP-45 consisting of 45 amino acids, high-molecular type γ-BNP having molecular weight of about 13,000 formed by cutting out a signal peptide from a BNP precursor and the like. Known C-type natriuretic peptides (CNP) are CNP-22 consisting of 22 amino acids, CNP-53 consisting of 53 amino acids extending to the N-terminal and the like. These natriuretic peptides act on kidneys, adrenalglands and vascular walls and play an important role in adjusting electrolytes in a general body fluid and blood pressure ("Peptides Adjusting Circulation and Related Diseases", p. 14–25, Youdosha, 1992).

α-ANP has a vasodilatory action and a diuretic action and is used as a therapeutic agent for cardiovascular diseases such as heart failure (Jpn. Pharmacol. Ther., 23, 949–952 (1995)).

In an ophthalmological field, it was reported that α-ANP exhibits an effect of lowering intraocular pressure (Curr. Eye Res., 6, 1189–1196 (1987)). However, other effects of α-ANP have scarcely been studied, and there have been no literature which reports effects of the natriuretic peptides on lacrimal gland and the keratoconjunctival disorders by instillating them.

Few application studies of the natriuretic peptides to the ophthalmological field have been done except for the study on the effect of lowering intraocular pressure. It is a very interesting subject to study new effects of the natriuretic peptides in the ophthalmological field.

DISCLOSURE OF THE INVENTION

Studying precisely in order to find new effects of natriuretic peptides in an ophthalmological field, the present inventors found that the natriuretic peptides exhibit effects of promoting lacrimal secretion and are useful as therapeutic agents for keratoconjunctival disorders.

The present invention relates to eyedrops for promoting the lacrimal secretion and treating the keratoconjunctival disorders containing the natriuretic peptide as an active ingredient.

The natriuretic peptides are atrial natriuretic peptides (ANP), brain natriuretic peptides (BNP) and C-type natriuretic peptides (CNP) in the present invention. ANP, BNP and CNP having different structures are known, and the natriuretic peptides of the present invention include all of them.

The natriuretic peptides are useful drugs as therapeutic agents for cardiovascular diseases, but few effects have been reported other than their effects of lowering intraocular pressure in an ophthalmological field.

Studying application of the natriuretic peptides to the ophthalmological field, the present inventors found that when the natriuretic peptides are instilled into rabbits, the natriuretic peptides exhibit excellent effects of promoting the lacrimal secretion. Details will be described in the part of "Pharmacological Test". Since the lacrimal fluid exhibits the effect of curing the keratoconjunctival disorders as described in detail in the part of "Background Art", the present drugs are expected to be useful as the therapeutic agents for the keratoconjunctival disorders. Typical examples of the keratoconjunctival disorder are dry eye, corneal erosion and corneal ulcer.

The eyedrops of the present invention can be prepared by dissolving the natriuretic peptide in a general ophthalmic vehicle in using the eyedrops. The eyedrops can be formulated by adding optionally a suitable amount of an isotonic agent such as sodium chloride or concentrated glycerin, a buffer such as sodium phosphate or sodium acetate, a surfactant such as polyoxyethylene sorbitan monooleate, polyoxyl 40 stearate or polyoxyethylene hydrogenated castor oil, a stabilizer such as sodium citrate or disodium edetate, a preservative such as benzalkonium chloride or paraben or the like. pH can be in the range acceptable to ophthalmic preparations and is preferably in the range of 4 to 8.

A concentration of the active ingredient in the eyedrops is 0.001 to 1% (W/V), preferably 0.005 to 0.5% (W/V), more preferably 0.05 to 0.5% (W/V). The eyedrops are administered by instilling one to several times per day.

BEST MODE FOR CARRYING OUT THE INVENTION

Formulation Example and Pharmacological Test are shown below as Examples.
1. Formulation Example
Typical formulation is shown below.
Formulation 1 (Preparation of 0.1% Eyedrops)
A natriuretic peptide (100 mg) was dissolved in physiological saline (100 ml) to prepare 0.1% eyedrops.
Further, varying the amount of the natriuretic peptide to be added, natriuretic peptide eyedrops having concentrations of 0.001%, 0.005%, 0.01%, 0.05%, 0.5% and 1.0% (W/V) were also prepared.
2. Pharmacological Test
The Schirmer test paper method, which is used for measurement of an amount of a human lacrimal fluid, is one method of measuring a change in an amount of a lacrimal fluid of a normal animal in instilling a drug. In the present invention, an amount of a lacrimal fluid in instilling the natriuretic peptide was measured by using the Schirmer test paper method, and an effect of the natriuretic peptide on a rate of lacrimal secretion was studied.
Experimental Method
Laboratory Animal
Male Japanese white rabbits, body weight; 1.8 to 2.2 kg, were used for the experiment.
Preparation of Solution of Test Drug
The natriuretic peptide (0.56 mg) was dissolved in sterile purified water to prepare a 0.1% solution just before using. This solution is referred to as a solution of a test drug.
Method of Administering Drug
The solution of the test drug (50 $\mu$l) was instilled into a left eye once. In order to study an effect of a vehicle (purified water) on the lacrimal secretion, the vehicle alone (50 $\mu$l) was instilled into a right eye once.
Method of Measurement
Amounts of the lacrimal fluid were measured using Schirmer test paper with respect to the eye to which the drug was administered and the eye to which no drug was administered before administering the drug and after a prescribed period of time from the instillation. One end of the Schirmer test paper was folded, and the folded end was inserted into a site of one third of palpebrae inferior toward a temporal side of the rabbit. One minute later, length of a wet portion (Schirmer value, mm) of the test paper was measured from the fold.
Three minutes before measuring the amount of the lacrimal fluid, a 0.4% ophthalmic solution of oxybuprocaine hydrochloride (10 $\mu$l), which is a local anesthetic, was instilled into both eyes once.
Results
The action of the solution of the test drug on the rate of the lacrimal secretion at a time of T hours after the instillation is represented by the increment of the lacrimal fluid (mm) determined by the following equation.

Increment of lacrimal fluid (mm)=[SM(D-T)−SM(D-0)]−[SM(V-T)−SM(V-0)]

SM(D-T): Schirmer value in the eye to which the drug was administered (left eye) T hours after administering the drug
SM(D-O): Schirmer value in the eye to which the drug was administered (left eye) before administering the drug
SM(V-T): Schirmer value in the eye to which the vehicle was administered (right eye) T hours after administering the vehicle
SM(V-O): Schirmer value in the eye to which the vehicle was administered (right eye) before administering the vehicle.

As examples of test results, Table 1 shows increments of the lacrimal fluid (mm) one hour after instilling solutions of test drugs (rat $\alpha$-ANP, rat BNP-32 and human CNP-22; all of them were purchased from Peptide Research Institute).

TABLE 1

| Measuring time | Increment of lacrimal fluid (mm) | | |
|---|---|---|---|
| | Rat $\alpha$-ANP | Rat BNP-32 | Human CNP-22 |
| One hour after administering drug | +1.92 | +2.08 | +1.33 |

The values in the table are respective averages of six samples per group.

As apparent from Table 1, the test drugs (rat $\alpha$-ANP, rat BNP-32 and human CNP-22) exhibit excellent effects of promoting the lacrimal secretion.

Industrial Applicability

The present invention can provide eyedrops containing a natriuretic peptide which exhibit an excellent effect of promoting lacrimal secretion and are useful as lacrimal secretion promoters and as therapeutic agents for keratoconjunctival disorders.

What is claimed is:
1. A method of treating a person having a keratoconjunctival disorder comprising administering an effective amount of a natriuretic peptide to at least one eye of said person.
2. The method of claim 1 wherein said keratoconjunctival disorder is dry eye.
3. The method of claim 1 wherein said keratoconjunctival disorder is corneal erosion.
4. The method of claim 1 wherein said keratoconjunctival disorder is a corneal ulcer.
5. The method of claim 1 wherein said natriuretic peptide is an atrial natriuretic peptide.
6. The method of claim 1 wherein said natriuretic peptide is a brain natriuretic peptide.
7. The method of claim 1 wherein said natriuretic peptide is a C-type natriuretic peptide.
8. The method of claim 1 wherein the natriuretic peptide is administered as eyedrops in a concentration of 0.001 to 1% (W/V).
9. The method of claim 1 wherein the natriuretic peptide is administered as eyedrops in a concentration of 0.005 to 0.5% (W/V).
10. The method of claim 1 wherein the natriuretic peptide is administered as eyedrops in a concentration of 0.05 to 0.5% (W/V).

* * * * *